US011051783B2

(12) United States Patent
Senegas et al.

(10) Patent No.: US 11,051,783 B2
(45) Date of Patent: Jul. 6, 2021

(54) X-RAY RADIOGRAPHY APPARATUS

(71) Applicant: KONINKLIJKE PHILIPS N.V., Eindhoven (NL)

(72) Inventors: Julien Senegas, Hamburg (DE); Sascha Andreas Jockel, Hamburg (DE); Hanns-Ingo Maack, Norderstedt (DE); Martin Bergtholdt, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/621,415

(22) PCT Filed: Jun. 15, 2018

(86) PCT No.: PCT/EP2018/066032
§ 371 (c)(1),
(2) Date: Dec. 11, 2019

(87) PCT Pub. No.: WO2018/229286
PCT Pub. Date: Dec. 20, 2018

(65) Prior Publication Data
US 2020/0100757 A1    Apr. 2, 2020

(30) Foreign Application Priority Data
Jun. 15, 2017  (EP) .................................... 17176201

(51) Int. Cl.
*A61B 6/00*  (2006.01)
*A61B 6/04*  (2006.01)
(Continued)

(52) U.S. Cl.
CPC ............... *A61B 6/584* (2013.01); *A61B 6/04* (2013.01); *A61B 6/06* (2013.01); *A61B 6/08* (2013.01);
(Continued)

(58) Field of Classification Search
CPC .............. A61B 6/584; A61B 6/04; A61B 6/06
See application file for complete search history.

(56) References Cited

U.S. PATENT DOCUMENTS

2009/0285357 A1    11/2009  Khamene
2015/0327821 A1    11/2015  Hu
(Continued)

FOREIGN PATENT DOCUMENTS

| WO | WO2014033614 A1 | 3/2014 |
| WO | WO2015081295 A1 | 6/2015 |
| WO | WO2016001130 A1 | 1/2016 |

OTHER PUBLICATIONS

PCT International Search Report, International application No. PCT/EP2018/066032, dated Sep. 17, 2018.
(Continued)

*Primary Examiner* — Hugh Maupin
(74) *Attorney, Agent, or Firm* — Larry Liberchuk (57) ABSTRACT

The present invention relates to an X-ray radiograph apparatus (10). It is described to placing (110) an X-ray source (20) relative to an X-ray detector (30) to form an examination region for the accommodation of an object, wherein, a reference spatial coordinate system is defined on the basis of geometry parameters of the X-ray radiography apparatus. A camera (40) is located (120) at a position and orientation to view the examination region. A depth image of the object is acquired (130) with the camera within a camera spatial coordinate system, wherein within the depth image pixel values represent distances for corresponding pixels. A processing unit (50) transforms (140), using a mapping function, the depth image of the object within the camera spatial coordinate system to the reference spatial coordinate system, wherein, the camera position and orientation have been calibrated with respect to the reference spatial coordinate system to yield the mapping function that maps a spatial
(Continued)

point within the camera spatial coordinate system to a corresponding spatial point in the reference spatial coordinate system. A synthetic image is generated (150) within the reference spatial coordinate system. The synthetic image is output (160) with an output unit (60).

15 Claims, 4 Drawing Sheets

(51) Int. Cl.
     *A61B 6/06*      (2006.01)
     *A61B 6/08*      (2006.01)
     *G06T 7/00*      (2017.01)
     *G06T 11/00*      (2006.01)

(52) U.S. Cl.
     CPC .............. *A61B 6/544* (2013.01); *A61B 6/585* (2013.01); *G06T 7/0012* (2013.01); *G06T 11/005* (2013.01)

(56) References Cited

U.S. PATENT DOCUMENTS

| | | |
|---|---|---|
| 2016/0058403 A1 | 3/2016 | Kim |
| 2016/0092078 A1 | 3/2016 | Braun |
| 2017/0007196 A1 | 1/2017 | Don |
| 2018/0008220 A1* | 1/2018 | Boone .................. A61B 8/4416 |
| 2019/0000564 A1* | 1/2019 | Navab .................... G06T 7/521 |

OTHER PUBLICATIONS

Horn B.K.P. et al., "Closed-Form Solution of Absolute Orientation Using Unit Quaternions", J. Optical Society of America A., vol. 4, No. 4, pp. 629-642, 1987.

Rusinkiewicz S. et al., "Efficient Variants of the ICP Algorithms", International Conference on 3D Digital Imaging and Modeling (3DIM), 2001.

* cited by examiner

X-RAY RADIOGRAPHY APPARATUS

FIELD OF THE INVENTION

The present invention relates to an X-ray radiography apparatus, to a method for providing imagery for an X-ray radiography apparatus, as well as to a computer program element and a computer readable medium.

BACKGROUND OF THE INVENTION

The general background of this invention is radiography. In radiography examinations, it is required to accurately position the patient with respect to the X-ray detector and to adapt the geometry configuration and system parameters to the patient anatomy. For example, the exposure chambers used for automatic exposure control (AEC) need to sit exactly behind the target anatomy. Similarly, the size of the collimation window needs to be adapted to fit the size of the body part to be imaged.

On current systems, it is state of the art to use visual markers (e.g. drawings of the exposure chambers on the detector cover) and visible light projected directly on the scene (detector, patient) as means to guide the operator. For example, the collimation window and the exposure chambers are projected using a light source and a slide-like device on the scene so that the operator can check the current settings by looking at the projected shape on the patient.

The current art has obvious limitations: not all required information is provided and the visibility of the projected light field can be very limited depending on the light conditions in the examination room and the clothes of the patient. Also, ideally, the operator needs to look at the patient from a position equivalent to the X-ray source to avoid any visual obstructions, which requires going iteratively back and forth between system configuration panel and observation point.

Other methods using regular video camera and overlays also suffer from geometric inaccuracy and obstructions since the video camera cannot be placed at the location of the X-ray source and oblique views of the scene are captured.

WO2015/081295A1 describes a system or method for improving quality in projection and tomographic x-ray, which includes a depth sensing device to measure a depth of at least one body part of a patient from the depth sensing device and a control unit to calculate a thickness and/or circumference of the body part using the depth information. The calculated thickness and circumference information is used to determine an optimal level of x-ray exposure for the body part. The system or method also includes a camera to identify the body part that needs to be examined and to detect any motion of the identified body part. However, there is a need to improve the imagery provided to an operator of an X-ray radiography apparatus.

WO 2016/001130 A1 describes a method for automatically configuring an X-ray imaging system for taking an X-ray image of an object. First, one or more depth images are obtained from one or more depth cameras covering at least an area covered by an X-ray bundle of an X-ray source. Then, a thickness of the object is determined from the depth image(s). Then, this thickness value is converted to a dose configuration of said X-ray imaging system by taking into account a transmission length of said X-ray bundle through said object and knowledge about tissue types being imaged.

SUMMARY OF THE INVENTION

It would be advantageous to have an improved apparatus for providing imagery to an operator of an X-ray radiography apparatus.

The object of the present invention is solved with the subject matter of the independent claims, wherein further embodiments are incorporated in the dependent claims. It should be noted that the following described aspects and examples of the invention apply also for the X-ray radiography apparatus, the method for providing imagery for an X-ray radiography apparatus, and for the computer program element and the computer readable medium.

According to a first aspect, there is provided an X-ray radiograph apparatus, comprising:
- an X-ray source;
- an X-ray detector;
- a camera;
- a processing unit; and
- an output unit.

The X-ray source is configured to be placed relative to the X-ray detector to form an examination region for the accommodation of an object. A reference spatial coordinate system is defined on the basis of geometry parameters of the X-ray radiography apparatus. The camera is configured to be located at a position and orientation to view the examination region and the camera is configured to acquire depth imagery within a camera spatial coordinate system, wherein within the depth imagery pixel values represent distances for corresponding pixels. The camera position and orientation have been calibrated with respect to the reference spatial coordinate system to yield a mapping function that maps a spatial point within the camera spatial coordinate system to a corresponding spatial point in the reference spatial coordinate system. The camera is configured to acquire a depth image of the object within the camera spatial coordinate system and provide the depth image to the processing unit. The processing unit is configured to use the mapping function to transform the depth image of the object within the camera spatial coordinate system to the reference spatial coordinate system and generate a synthetic image within the reference spatial coordinate system. The output unit is configured to output the synthetic image.

In this way an image of an object, such as a human subject, can be presented to an operator as if the image had been acquired by a camera located at the position of the X-ray source and not by a camera at the actual position of the camera. Alternatively, an image of the object can be presented to the operator as if the image had been acquired by a camera located at another position to the X-ray source if required. Thus, optimum and efficient positioning of the object within the examination region is facilitated, where parallax effects have been mitigated. In this manner, a patient can be positioned accurately with respect to the X-ray detector and the X-ray apparatus geometry configuration and system parameters can be appropriately adapted to the patient anatomy. Thus, because the operator is provided with the imagery of the position of the patient within the examination region as seen by the X-ray source, the operator can ensure that the exposure chambers used for automatic exposure control sit exactly behind the patient's anatomy. Furthermore, the operator can optimally adjust the X-ray source collimation window to fit the size of the object (patient's body part).

In the first aspect, the X-ray source has a collimator configured to confine the extent of the X-rays and wherein the processing unit is configured to generate a representation of the extent of the X-rays within the reference spatial coordinate system, and wherein the processing unit is configured to generate the synthetic image with the representation of the extent of the X-rays.

In other words, the X-ray source has a collimation window and the synthetic image has superimposed upon it an indication of the size of the collimation window at the object. In this manner, the operator can move the object within the examination region and/or vary the size of the collimation window in order to provide an optimum radiography examination.

In the first aspect, the processing unit is configured to generate the synthetic image having the representation of the extent of X-rays at the position of the object.

In other words, the X-ray source is configured to emit X-rays over an angular and spatial spread, and the processing unit is configured to generate the synthetic image having a representation of the extent of the spread of X-rays at the position of the object. Thus the operator is not only provided with an indication of the size of the collimation window from the perspective of the X-ray source, but is provided with what the size of that window is at the object. This takes into account objects, or parts of objects, that are very close to the X-ray detector and objects that are further away from the detector.

In an example, the X-ray detector has at least one exposure chamber configured to measure an exposure level of X-rays and wherein the processing unit is configured to generate a representation of the extent of the at least one exposure chamber within the reference spatial coordinate system. The processing unit is configured then to generate the synthetic image having a representation of the extent of the at least one exposure chamber.

In this manner, the operator can ensure that the object (e.g. patient) is correctly positioned with respect to exposure chambers used for automatic exposure control that takes into account the actual path X-rays will take from the X-ray source to the detector because he synthetic image is acquired from the perspective of the X-ray source and its relationship to the X-ray detector.

In an example, the processing unit is configured to generate the synthetic image having the representation of the extent of the at least one exposure chamber at the position of the object.

In an example, the X-ray detector has an active area configured to detect X-rays and wherein the processing unit is configured to generate a representation of the extent of the active area within the reference spatial coordinate system. The processing unit is configured then to generate the synthetic image having the representation of the extent of the active area.

In an example, the processing unit is configured to generate the synthetic image having the representation of the extent of the active area at the position of the object. In an example, the X-ray detector has a lateral and longitudinal axis and wherein the processing unit is configured to generate a representation of the lateral axis and/or longitudinal axis within the reference spatial coordinate system. The processing unit is configured then to generate the synthetic image having the representation of the lateral axis and/or longitudinal axis.

In this way, the operator is provided with further means to help enable the correct alignment of the object (e.g. patient) with the apparatus.

In other words, a symmetry axis for the X-ray detector is useable to check that the patient is well aligned with respect to the X-ray detector.

In an example, the camera is configured to acquire a 2D image and provide that image to the processing unit, and wherein the processing unit is configured to generate the synthetic image comprises utilization of the 2D image.

In this way, a synthetic image with realistic texture can be generated.

Thus, although the depth image can be considered to be a 2D image, because it has two dimensions, here an additional image to the depth image is acquired, that could for example be either multi-channel (color) or single-channel (monochrome), where the pixel values represent another property of the scene than depth, for example: amount of reflected light in a given spectral range; and a thermo-image.

According to a second aspect, there is provided a method (100) for providing imagery for an X-ray radiograph apparatus, comprising:

a) placing an X-ray source relative to an X-ray detector to form an examination region for the accommodation of an object, wherein, a reference spatial coordinate system is defined on the basis of geometry parameters of the X-ray radiography apparatus;

b) locating a camera at a position and orientation to view the examination region;

c) acquiring a depth image of the object with the camera within a camera spatial coordinate system, wherein within the depth image pixel values represent distances for corresponding pixels;

d) transforming, with a processing unit using a mapping function, the depth image of the object within the camera spatial coordinate system to the reference spatial coordinate system, wherein, the camera position and orientation have been calibrated with respect to the reference spatial coordinate system to yield the mapping function that maps a spatial point within the camera spatial coordinate system to a corresponding spatial point in the reference spatial coordinate system;

i) generating a synthetic image within the reference spatial coordinate system; and j) outputting the synthetic image with an output unit.

In the second aspect, the X-ray source has a collimator configured to confine the extent of the X-rays; and wherein the method comprises step (e) generating with the processing unit a representation of an extent of the X-rays within the reference spatial coordinate system, and wherein step i) comprises generating the synthetic image with the representation of the extent of the X-rays.

In the second aspect, step i) comprises generating the synthetic image having the representation of the extent of the X-rays at the position of the object.

In an example, the X-ray detector has at least one exposure chamber configured to measure an exposure level of X-rays; and wherein the method comprises step (f) generating with the processing unit a representation of an extent of the at least one exposure chamber within the reference spatial coordinate system, and wherein step i) comprises generating the synthetic image having the representation of the extent of the at least one exposure chamber.

In an example, the X-ray detector has an active area configured to detect X-rays, and wherein the method comprises step (g) generating with the processing unit a representation of an extent of the active area within the reference spatial coordinate system, and wherein step i) comprises generating the synthetic image having the representation of the extent of the active area.

According to another aspect, there is provided a computer program element controlling a device and/or system as previously described which, if the computer program element is executed by a processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
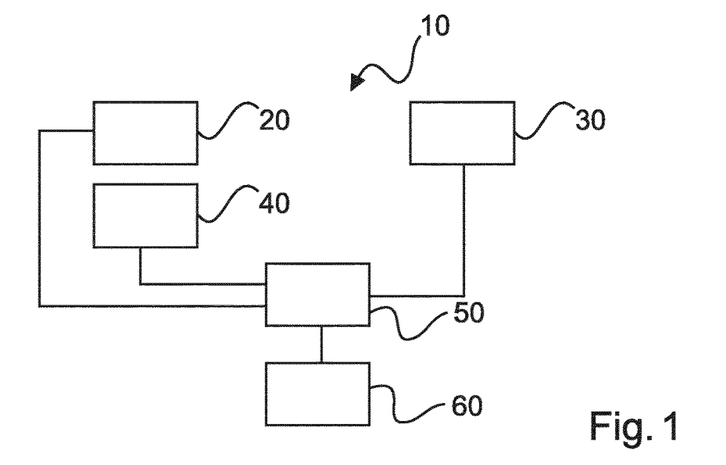
FIG. 1 shows a schematic set up of an example of an X-ray radiography apparatus.

FIG. 1 shows an example of an X-ray radiograph apparatus 10. The X-ray radiography apparatus comprises an X-ray source 20, an X-ray detector 30, a camera 40, a processing unit 50, and an output unit 60. The X-ray source 20 is configured to be placed relative to the X-ray detector 30 to form an examination region for the accommodation of an object. A reference spatial coordinate system is defined on the basis of geometry parameters of the X-ray radiography apparatus 10. The camera 40 is configured to be located at a position and orientation to view the examination region and the camera 40 is configured to acquire depth imagery within a camera spatial coordinate system, wherein within the depth imagery pixel values represent distances for corresponding pixels. The camera position and orientation have been calibrated with respect to the reference spatial coordinate system to yield a mapping function that maps a spatial point within the camera spatial coordinate system to a corresponding spatial point in the reference spatial coordinate system. The camera 40 is configured to acquire a depth image of the object within the camera spatial coordinate system and provide the depth image to the processing unit 50. The processing unit 50 is configured to use the mapping function to transform the depth image of the object within the camera spatial coordinate system to the reference spatial coordinate system and generate a synthetic image within the reference spatial coordinate system. The output unit 60 is configured to output the synthetic image.

In an example, the mapping function maps a spatial point within the reference spatial coordinate system to a corresponding spatial point in the camera spatial coordinate system.

In an example, the geometry parameters of the X-ray radiography system used to define the reference spatial coordinate system comprises one or more of: a position of the X-ray source relative to the X-ray detector; geometry parameters related to the Source-Image Receptor Distance (SID); the height of the X-ray detector; the width of the X-ray detector; the height of the X-ray source; the width of the X-ray source; the rotation angle of the X-ray source; longitudinal and lateral positions of the X-ray detector; longitudinal and lateral positions of the X-ray source; rotation angles (roll, pitch, yaw) of the X-ray detector and/or of the X-ray source. In this way, the X-ray detector can be fully defined within the reference spatial coordinate system, and the X-ray source can be fully defined within the reference spatial coordinate system.

In an example, the camera in addition to acquiring the depth image is also configured to acquire a "regular" image of the scene, either in colour such as R, G, or B colorspace, or in gray scale (monochrome or infrared). In an example, the camera is configured to acquire 3D, Depth (aka range) data image, and from the depth data image, 3D point coordinates can be computed using the intrinsic parameters of the camera system. In an example, the regular image is used to generate the synthetic image on which the overlays are shown. A correspondence (mapping function) between the Pixels in the regular image and the depth image is used. This is needed because the regular image can be acquired by another sensor than the depth sensor, with both having different positions and orientations. This is however a standard problem in computer vision and in nowadays 3D camera systems, and this mapping can be provided by the manufacturer of the 3D camera system. However, in an example the regular image is acquired by a regular camera that is not a fixed element of the 3D camera system, in which case this mapping function needs to be computed once, and is known as calibration of the camera system. It is also to be noted that more than one additional regular images may be used, such as RGB and infrared.

Thus, the camera can acquire a single depth image and from this depth image 3D points, meaning 3D spatial coordinates of points, can be computed. The 3D point coordinates of the object within this image can be used to enable a transformation from the camera spatial coordinate system to the reference spatial coordinate system to be undertaken. Furthermore, the depth image and the computed 3D points can be used to provide a representation of the 3D points using for example point clouds. Thus in effect the depth image can be used to provide a 3D image. A 2D projection of that 3D image can then be used in generating the synthetic image in the reference spatial coordinate system. Alternatively, the camera can acquire a second 2D image (regular image) at the same time as acquiring the depth image. The depth image is used as discussed above to enable transformation from the camera spatial coordinate system to the reference spatial coordinate system and the regular image is used to generate the synthetic image in the reference spatial coordinate system (for example from the viewpoint of the X-ray source), upon which for example overlays can be shown.

Typically, this requires two different sensors integrated in the camera system. It can be a single one in case of infrared only.

In an example, the camera uses a time-of-flight technique such as LIDAR to determine the 3D imagery. In an example, the camera uses structured light to determine the 3D imagery. In an example the term "a camera" actually refers to two or more 2D cameras that are used together to provide 3D imagery, such as a stereoscopic system.

According to an example, the X-ray source has a collimator configured to confine the extent of the X-rays and wherein the processing unit is configured to generate a representation of the extent of the X-rays within the reference spatial coordinate system. The processing unit is configured then to generate the synthetic image with the representation of the extent of the X-rays.

According to an example, the processing unit is configured to generate the synthetic image having the representation of the extent of X-rays at the position of the object.

According to an example, the X-ray detector has at least one exposure chamber configured to measure an exposure level of X-rays and wherein the processing unit is configured to generate a representation of the extent of the at least one exposure chamber within the reference spatial coordinate system. The processing unit is configured then to generate the synthetic image having a representation of the extent of the at least one exposure chamber.

According to an example, the processing unit is configured to generate the synthetic image having the representation of the extent of the at least one exposure chamber at the position of the object.

According to an example, the X-ray detector has an active area configured to detect X-rays and wherein the processing unit is configured to generate a representation of the extent of the active area within the reference spatial coordinate system. The processing unit is configured then to generate the synthetic image having the representation of the extent of the active area.

According to an example, the processing unit is configured to generate the synthetic image having the representation of the extent of the active area at the position of the object.

According to an example, the X-ray detector has a lateral and longitudinal axis and wherein the processing unit is configured to generate a representation of the lateral axis and/or longitudinal axis within the reference spatial coordinate system. The processing unit is configured then to generate the synthetic image having the representation of the lateral axis and/or longitudinal axis.

According to an example, the camera is configured to acquire a 2D image and provide that image to the processing unit. The processing unit is configured then to generate the synthetic image comprises utilization of the 2D image.

In an example, the 2D image is a monochrome image. In an example, the 2D image is a colour image.

Figure 2:
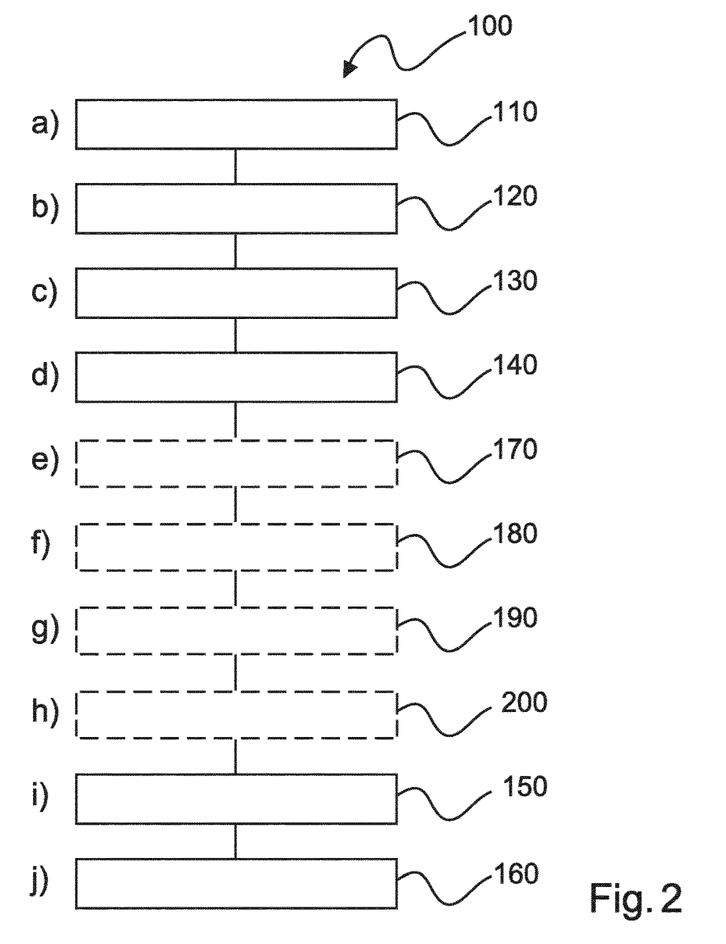
FIG. 2 shows a method for providing imagery for an X-ray radiography apparatus.

FIG. 2 shows a method 100 for providing imagery for an X-ray radiograph apparatus in it basic steps. The method 100 comprises:

in a placing step 110, also referred to as step (a), placing an X-ray source 20 relative to an X-ray detector 30 to form an examination region for the accommodation of an object, wherein, a reference spatial coordinate system is defined on the basis of geometry parameters of the X-ray radiography apparatus;

in a locating step 120, also referred to as step (b), locating a camera 40 at a position and orientation to view the examination region;

in an acquiring step 130, also referred to as step (c), acquiring a depth image of the object with the camera within a camera spatial coordinate system, wherein within the depth image pixel values represent distances for corresponding pixels;

in a transforming step 140, also referred to as step (d), transforming, with a processing unit 50 using a mapping function, the depth image of the object within the camera spatial coordinate system to the reference spatial coordinate system, wherein, the camera position and orientation have been calibrated with respect to the reference spatial coordinate system to yield the mapping function that maps a spatial point within the camera spatial coordinate system to a corresponding spatial point in the reference spatial coordinate system;

in a generating step 150, also referred to as step (i), generating a synthetic image within the reference spatial coordinate system; and in an outputting step 160, also referred to as step (j), outputting the synthetic image with an output unit 60.

According to an example, the X-ray source has a collimator configured to confine the extent of the X-rays; and wherein the method comprises step (e) generating 170 with the processing unit a representation of an extent of the X-rays within the reference spatial coordinate system, and wherein step i) comprises generating the synthetic image with the representation of the extent of the X-rays.

According to an example, step i) comprises generating the synthetic image having the representation of the extent of the X-rays at the position of the object.

In an example, generating the representation of the extent of the X-rays comprises utilisation of a ray tracing algorithm.

According to an example, the X-ray detector has at least one exposure chamber configured to measure an exposure level of X-rays; and wherein the method comprises step (f) generating 180 with the processing unit a representation of an extent of the at least one exposure chamber within the reference spatial coordinate system, and wherein step i) comprises generating the synthetic image having the representation of the extent of the at least one exposure chamber.

In an example, step i) comprises generating the synthetic image having the representation of the extent of the at least one exposure chamber at the position of the object. In an example, generating the representation of the extent of the at least one exposure chamber comprises utilisation of a ray tracing algorithm.

According to an example, the X-ray detector has an active area configured to detect X-rays, and wherein the method comprises step (g) generating 190 with the processing unit a representation of an extent of the active area within the reference spatial coordinate system, and wherein step i) comprises generating the synthetic image having the representation of the extent of the active area.

In an example, step i) comprises generating the synthetic image having the representation of the extent of the active area at the position of the object.

In an example, generating the representation of the extent of the active area comprises utilisation of a ray tracing algorithm.

In an example, the X-ray detector has a lateral and longitudinal axis and wherein the method comprises step (h) generating 200 with the processing unit a representation of the lateral axis and/or longitudinal axis within the reference spatial coordinate system, and wherein step i) comprises generating the synthetic image having the representation of the lateral axis and/or longitudinal axis In an example, the camera is configured to acquire a 2D image and the method comprises providing that image to the processing unit, and wherein step i) comprises utilization of the 2D image.

Figure 3:
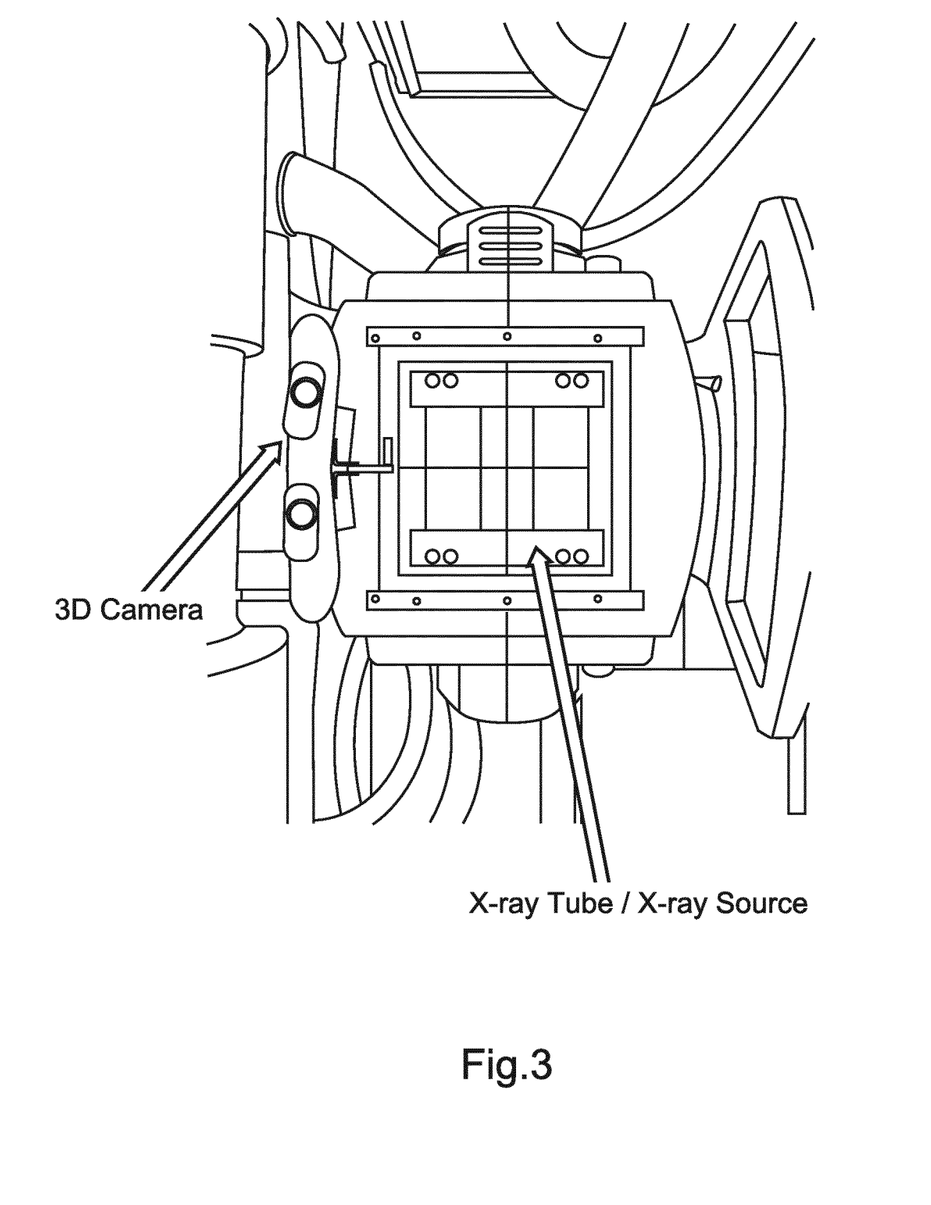
FIG. 3 shows an example of an X-ray source (X-ray tube) with a 3D camera mounted on the X-ray tube support.
Figure 4:
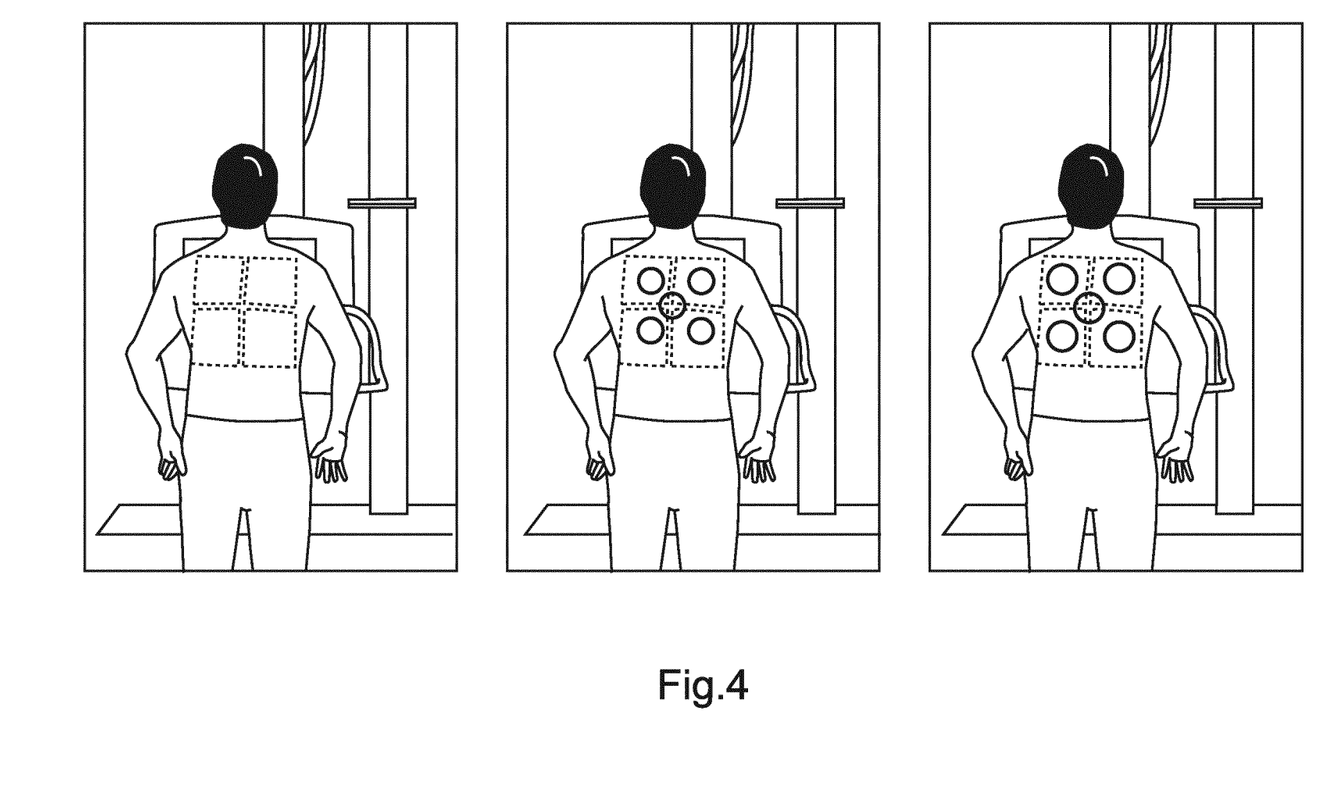
FIG. 4 shows images with and without overlays and overlays that in one image have undergone geometric correction.
Figure 5:
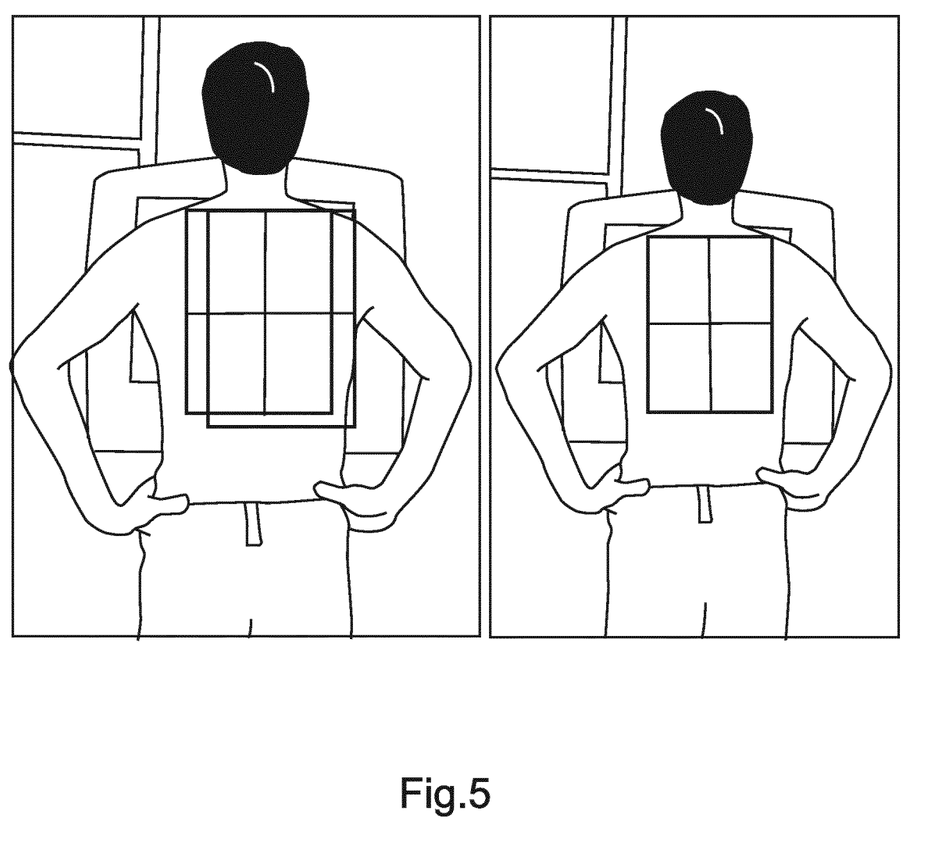
FIG. 5 shows images with overlays that have not undergone geometric correction and also that have undergone geometric correction.

The X-ray radiography apparatus and method for providing imagery for an X-ray radiography apparatus, are now described in more detail in conjunction with FIGS. 3-5.

A depth camera that can acquire 3D imagery, 3D computer vision methods, and a display are used to show to the operator an augmented-reality, synthesized image with high geometry accuracy, according to the following steps:

A depth camera, providing depth data and regular video data at suitable frame rate, is positioned so as to image the examination area with minimal obstruction, e.g. on top of the collimator. An example of a 3D camera (depth camera) mounted on the X-ray source (X-ray tube) is shown in FIG. 3.

The camera position and orientation have been calibrated with respect to the geometry of the radiography system. This procedure yields a mapping function that, in combination with the real-time value of the geometry parameters of the radiography system, allows transforming point coordinates from the camera coordinate system into the X-ray reference coordinate system.

In the next step, a synthesized image showing the patient, and, as digital overlays, geometrically accurate position and shape of e.g. exposure chambers, collimation window, and active area of detector, is reconstructed using known computer vision methods and the coordinate transformation obtained above.

Thus, a synthesized image as seen from the X-ray source is reconstructed from the depth image, but the synthesized image can be reconstructed from other vantage points and is not required to be that as seen from the X-ray source. The overlays are generated on the scene by applying a central projection with the X-ray source as center.

The synthesized image representing the projection of the patient onto the X-ray detector can also be generated from the depth image. The overlays are then generated by computing size, shape, and position of the different patterns projected on the X-ray detector plane.

The augmented-reality, synthesized image is shown to the operator on a display. Different colors can be used to represent each of the different overlay types.

FIG. 4 shows an example of an overlay for exposure chambers and collimation window that can be generated using the depth data captured by a 3D camera. Three pictures are shown in FIG. 4. The left hand picture shows an image acquired by the 3D camera. In the centre picture overlays of the exposure chambers and collimation window are shown as viewed from the 3D camera's perspective i.e., in the camera spatial coordinate system, without applying the proposed mapping function. In the right hand picture the overlays have been geometrically corrected based on the mapping function derived from the calibration of the camera and the geometry parameters of the X-ray radiography apparatus and are now precisely located at the correct pixel positions.

FIG. 5 shows images with an overlay of the collimation that have not been subject to correction on the left and that have been corrected on the right. The image on the left shows the 3D scene seen from the camera. Due to the camera being positioned to the side of the X-ray source, the position and size of the collimation overlay (the rectangles projected onto the subject's back) depend on the distance to the X-ray source that is chosen as reference. This is represented by the two different rectangles. Following transformation from the camera spatial coordinate system to the reference spatial coordinate system, as shown in the image on the right, the 3D scene is now shown as seen from the X-ray source. The position and size of the collimation overlay are now independent of the distance to the X-ray source chosen as reference and furthermore accurately match the position and size obtained using a light projector.

Camera Calibration

In general, it is desired to express the coordinates of a 3D point in a coordinate system that is specified with respect to the examination room, or, with respect to the medical imaging system or X-ray radiography apparatus. In the following, this reference spatial coordinate system is referred to as the "world" coordinate system, as opposed to the camera spatial coordinate system.

The extrinsic camera parameters describe the transformation from a 3D point $P_w$ in the world coordinate system to a 3D point $P_c$ in the camera coordinate system. These are given by:

$$P_w = \begin{pmatrix} X_w \\ Y_w \\ Z_w \end{pmatrix}$$

$$P_c = \begin{pmatrix} X_c \\ Y_c \\ Z_c \end{pmatrix}$$

Denoting R and T the rotation and translation defining the extrinsic camera parameters, the following relation holds:

$$\begin{pmatrix} X_c \\ Y_c \\ Z_c \end{pmatrix} = R \begin{pmatrix} X_w \\ Y_w \\ Z_w \end{pmatrix} + T$$

The translation vector T can be seen as the coordinates of the origin of the world coordinate system, expressed in the camera coordinate system. Each column of the rotation matrix denotes the coordinates (in camera coordinate system) of the unit vectors oriented along the main axes of the world coordinate system.

In order to determine the extrinsic parameters for a given camera position and orientation, the following approach can be used. In this approach, it is assumed that the intrinsic parameters of the camera, that define the mapping of a 2D point in image coordinates to a 3D point in camera coordinates, are already known. These can be computed using known methods, for example based on images of a checkerboard pattern. See for example:
http://docs.opencv.org/2.4/doc/tutorials/calib3d/camera-_calibration/camera_calibration.html.

First, a depth image of a known object is acquired with the camera. In this image, a number of calibration points with known coordinates in the world coordinate system are determined. These points can be for example located at specific, known positions of the world coordinate system, such as the corners of the detector front cover. These calibration points compose a calibration dataset consisting of N pairs $(P_c^i, P_w^i)$, $0 \leq i < N$, leading to a set of N equations of the type: $P_c^i = R \cdot P_w^i + T$. This linear system can then be solved for the unknown coefficients of the rotation matrix R and of the translation vector T. Examples of computation algorithms can be found in: Berthold K. P. Horn. Closed-form solution of absolute orientation using unit quaternions. J. Opt. Soc. Am. A. Vol. 4, No. 4, 629-642, 1987.

Increased robustness can be obtained if a number N>3 is used (system is over-determined) and if the calibration points are not co-planar.

Other approaches can be used. For example, instead of using a set of well-defined calibration points, a point cloud describing the world coordinates such as a reference 3D object with known pattern (for example: parts of the detector front cover) can be used. Candidate calibration points, likely to be located on the reference object, are first extracted from the acquired image using for example an edge detector. Then, the matching between these candidate calibration points and the reference 3D point cloud in world coordinates, together with the unknown rotation matrix R and translation vector T can be computed using the iterative closest point algorithm as described in Rusinkiewicz et al: Szymon Rusinkiewicz and Marc Levoy. Efficient Variants of the ICP algorithms. International Conference on 3D Digital Imaging and Modeling (3DIM), 2001.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments. The computer program or the output unit may be integrated into an imaging or an navigation system.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray radiography apparatus, comprising:
an X-ray source that includes a collimator configured to confine an extent of X-rays;
an X-ray detector configured to be placed relative to the X-ray source to form an examination region for accommodating an object;
a camera configured to be located at a position and orientation to view the examination region and acquire depth imagery within a camera spatial coordinate system, wherein pixel values represent distances for corresponding pixels within the depth imagery, wherein the position and orientation of the camera are calibrated with respect to a reference spatial coordinate system to yield a mapping function that maps a spatial point within the camera spatial coordinate system to a corresponding spatial point in a reference spatial coordinate system, the reference spatial coordinate system being defined based on geometry parameters of the X-ray radiography apparatus, and wherein the camera is configured to acquire a depth image of the object within the camera spatial coordinate system;
processor circuitry configured to:
use the mapping function to transform the depth image of the object within the camera spatial coordinate system to the reference spatial coordinate system;
generate a synthetic 2D (two dimensional) image within the reference spatial coordinate system;
generate a representation of the extent of the X-rays within the reference spatial coordinate system; and
generate the synthetic 2D image with the representation of the extent of the X-rays at the position of the object by utilizing one of the depth image and a 2D regular image acquired by the camera; and
an output configured to output the synthetic 2D image.

2. The apparatus according to claim 1, wherein the X-ray detector comprises at least one exposure chamber configured to measure an exposure level of X-rays, wherein the processor circuitry, is configured to:
generate a representation of the extent of the at least one exposure chamber within the reference spatial coordinate system, and
generate the synthetic 2D image including a representation of the extent of the at least one exposure chamber.

3. The apparatus according to claim 2, wherein the processor circuitry is configured to generate the synthetic 2D image including the representation of the extent of the at least one exposure chamber at the position of the object.

4. The apparatus according to claim 1, wherein the X-ray detector includes an active area configured to detect X-rays, wherein the processor circuitry is configured to generate a representation of the extent of the active area within the reference spatial coordinate system and generate the synthetic 2D image including the representation of the extent of the active area.

5. The apparatus according to claim 4, wherein the processor circuitry is configured to generate the synthetic 2D image including the representation of the extent of the active area at the position of the object.

6. The apparatus according to claim 1, wherein the X-ray detector includes a lateral and longitudinal axis, and wherein the processor circuitry is configured to generate a representation of at least one of the lateral axis and longitudinal axis within the reference spatial coordinate system and generate the synthetic 2D image including the representation of at least one of the lateral axis and longitudinal axis.

7. The apparatus according to claim 1, wherein the generation of the synthetic 2D image comprises both utilization of the depth image and utilization of a 2D regular image acquired by the camera.

8. The apparatus according to claim 1, wherein the position and orientation of the camera are calibrated with respect to the reference spatial coordinate system to yield the mapping function that maps the spatial point within the camera spatial coordinate system to the corresponding spatial point in the reference spatial coordinate system in combination with a real-time value of the geometry parameters of the X-ray radiography apparatus.

9. The apparatus according to claim 8, wherein the mapping function allows transforming point coordinates from the camera spatial coordinate system into the reference spatial coordinate system.

10. The apparatus according to claim 1, wherein the position and size of a collimation overlay projected onto a subject are independent of the distance to the X-ray source.

11. The apparatus according to claim 1, wherein the position and size of a collimation overlay projected onto a subject match the position and size of the collimation overlay obtained using a light projector.

12. A method for providing imagery for an X-ray radiography apparatus, comprising:
   placing an X-ray source relative to an X-ray detector to form an examination region for accommodating an object, wherein the X-ray source includes a collimator configured to confine an extent of X-rays, and wherein a reference spatial coordinate system is defined based on geometry parameters of the X-ray radiography apparatus;
   locating a camera at a position and orientation to view the examination region;
   acquiring a depth image of the object with the camera within a camera spatial coordinate system, wherein pixel values represent distances for corresponding pixels within the depth image;
   transforming, by processor circuitry using a mapping function, the depth image of the object within the camera spatial coordinate system to a reference spatial coordinate system, wherein the position and orientation of the camera are calibrated with respect to the reference spatial coordinate system to yield the mapping function that maps a spatial point within the camera spatial coordinate system to a corresponding spatial point in the reference spatial coordinate system;
   generating a representation of an extent of the X-rays within the reference spatial coordinate system;
   generating a synthetic 2D (two dimensional) image within the reference spatial coordinate system with the representation of the extent of the X-rays at the position of the object by utilizing one of the depth image and a 2D regular image acquired by the camera; and
   outputting the synthetic 2D image.

13. The method according to claim 12, wherein the X-ray detector includes at least one exposure chamber configured to measure an exposure level of X-rays; and further comprising generating a representation of an extent of the at least one exposure chamber within the reference spatial coordinate system, and generating the synthetic 2D image having the representation of the extent of the at least one exposure chamber.

14. The method according to claim 12, wherein the X-ray detector includes an active area configured to detect X-rays, and further comprising generating a representation of an extent of the active area within the reference spatial coordinate system, and generating the synthetic 2D image having the representation of the extent of the active area.

15. A non-transitory computer-readable medium having one or more executable instructions stored thereon which, when executed by at least one processor, cause the at least one processor to perform a method for providing imagery for an X-ray radiography apparatus, the method comprising:
   placing an X-ray source relative to an X-ray detector to form an examination region for accommodating an object, wherein the X-ray source includes a collimator configured to confine an extent of X-rays, and wherein a reference spatial coordinate system is defined based on geometry parameters of the X-ray radiography apparatus;
   locating a camera at a position and orientation to view the examination region;
   acquiring a depth image of the object with the camera within a camera spatial coordinate system, wherein pixel values represent distances for corresponding pixels within the depth image;
   transforming, by processor circuitry using a mapping function, the depth image of the object within the camera spatial coordinate system to a reference spatial coordinate system, wherein the position and orientation of the camera are calibrated with respect to the reference spatial coordinate system to yield the mapping function that maps a spatial point within the camera spatial coordinate system to a corresponding spatial point in the reference spatial coordinate system;
   generating a representation of an extent of the X-rays within the reference spatial coordinate system;
   generating a synthetic 2D (two dimensional) image within the reference spatial coordinate system with the representation of the extent of the X-rays at the position of the object by utilizing one of the depth image and a 2D regular image acquired by the camera; and
   outputting the synthetic 2D image.

\* \* \* \* \*